United States Patent [19]

Andrews

[11] 4,249,898
[45] Feb. 10, 1981

[54] ORTHODONTIC ROTATION SPRING
[75] Inventor: Lawrence F. Andrews, La Jolla, Calif.
[73] Assignee: "A"-Company, Inc., San Diego, Calif.
[21] Appl. No.: 92,871
[22] Filed: Nov. 9, 1979
[51] Int. Cl.³ .............................................. A61C 7/00
[52] U.S. Cl. .................................................. 433/21
[58] Field of Search ............................ 433/18, 21, 22
[56] References Cited
U.S. PATENT DOCUMENTS
2,381,128  8/1945  Laskin .................................. 433/21
3,414,976  12/1968  Steiner .................................. 433/21

Primary Examiner—Robert Peshock
Attorney, Agent, or Firm—Townsend & Townsend

[57] ABSTRACT

An orthodontic rotation spring, geometrically shaped as a "U" or an "S", that terminates at one end in a tube for the passage and retention of a tie wire, and at the other end with a curved surface. The entire spring is dimensioned for compression between an arch wire attached to an orthodontic bracket and a tooth band. A force vector results which acts to rotate the tooth about its axis.

6 Claims, 4 Drawing Figures

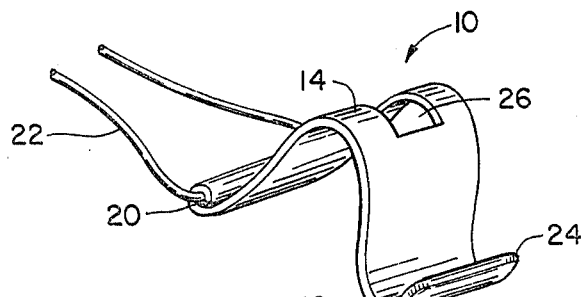
FIG._1.
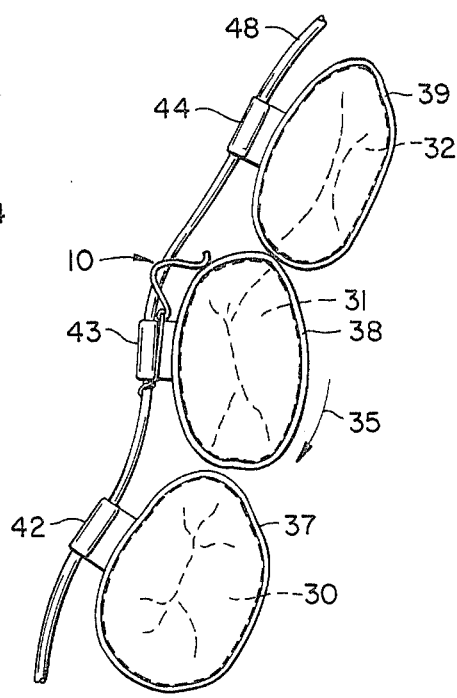
FIG._2.
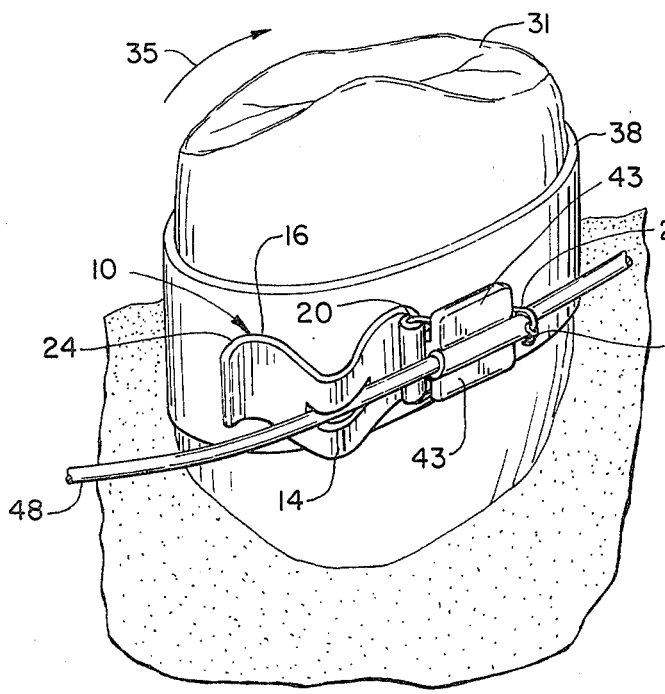
FIG._3.
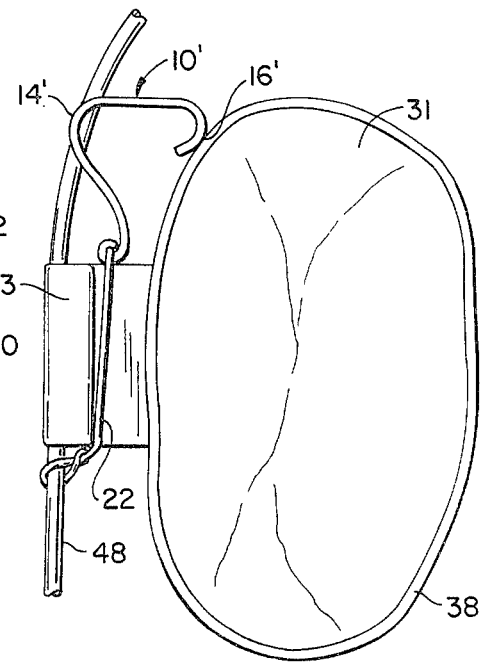
FIG._4.

ORTHODONTIC ROTATION SPRING

BACKGROUND OF THE INVENTION

This invention provides an orthodontic rotation spring for rotating a selected tooth about its axis.

It is a common technique of orthodontia to anchor an arch wire to two or more teeth in the mouth, and stress the arch wire at one or more points in order to effect a realignment of preselected teeth. A separate tooth band is typically cemented around each of several teeth, orthodontic brackets having been welded to each respective tooth band. An arch wire is fastened to and interconnects the orthodontic brackets.

One way of applying the required stress to a given tooth is to supply a spring which is anchored to the orthodontic bracket, and bears against the tooth (and typically against the arch wire as well). Many prior art spring devices have the problem that there is a terminating surface in proximity to the wearer's cheek or lip. This can cause irritation and discomfort to the wearer.

A further difficulty encountered with many prior art rotation springs is the lack of positive positioning. Thus, the spring is subject to movement perpendicular to the arch wire, which movement may unduly stress the spring mounting at the orthodontic bracket.

Yet another difficulty with many prior art springs is that they are relatively expensive to manufacture, as for example if they incorporate multiple parts that must be welded together. This can also result in additional points for potential failure.

Accordingly, there is a need for an orthodontic rotation spring which terminates away from the wearer's cheek or lip, is not subject to motion perpendicular to the arch wire, and which is simple to manufacture.

SUMMARY OF THE INVENTION

The invention is an orthodontic rotation spring that is extremely simple and inexpensive to manufacture, convenient to install, provides for extremely positive positioning, and has no terminating surface in proximity to the wearer's cheek or lip.

The orthodontic spring has an "S" or "U" configuration in which one end terminates in a tube for passing through and carrying a tie wire for fastening to the orthodontic bracket. The other end terminates in a curved surface against the tooth or tooth band for stressing the tooth in order to rotate the tooth about its axis. A curved surface between the tube and the curved surface proximate the tooth bears against the wearer's arch wire, and a notch in the rotation spring is preferably provided for positioning the spring against the arch wire to eliminate motion perpendicular to the wire.

The spring is preferably unitary in construction, being fabricated from a single piece of sheet metal. This eliminates the need for welding multiple pieces together, thereby substantially reducing fabrication costs and eliminating possible areas of failure.

The notch in the spring for positioning the rotation spring against the arch wire also facilitates installation as the tie wire holding the spring to the orthodontic bracket is tightened. This also facilitates a reproducible replacement of the spring should it be necessary to remove it.

Other objects, features and advantages of thi invention will become apparent after a reading of the remainder of the specification and the attached drawings.

BRIEF DESCRIPTION OF THE DRAWINGS

FIG. 1 is a perspective view of the preferred embodiment of the invention.

FIG. 2 is a top view of the spring of FIG. 1 in place within a wearer's mouth to effect a rotation of a selected tooth.

FIG. 3 is an enlarged perspective view of the present invention as applied to a tooth in a wearer's mouth.

FIG. 4 is a top view of an alternate embodiment of the invention as applied to a tooth in a wearer's mouth.

DESCRIPTION OF THE PREFERRED EMBODIMENT

The construction of the orthodontic rotation spring is best seen by reference to FIG. 1. Spring 10 is a sheet metal member configured to an "S"-shaped contour having oppositely facing convex curved surfaces 14 and 16. The curvature is generally cylindrical. The end of spring 10 closest to curved surface 14 is provided with a tie wire tube 20. Tie wire 22 passes through and is carried by tie wire tube 20. The end of spring 10 closest to curved surface 16 terminates at 24. Curved surface 14 has a central aperture 26 which extends far enough toward curved surface 16 and tie wire tube 20 to define a notch, the purpose of which will be seen more clearly below.

FIG. 2 shows a typical installation in a user's mouth having teeth 30, 31, and 32, with tooth 31 requiring a rotation about its axis in the sense of arrow 35. Teeth 30–32 have respective tooth bands 37, 38 and 39 to which respective orthodontic brackets 42, 43 and 44 are mounted in the conventional way. An arch wire 48 is shown installed in orthodontic brackets 42–44.

Rotation spring 10 is shown installed between arch wire 48 and tooth band 38 of tooth 31, to exert a force between arch wire 48 and tooth band 38 in order to rotate tooth 31 about its axis in the direction of arrow 35.

The mounting and positioning of orthodontic rotation spring 10 is best seen by reference to FIG. 3. Spring 10 is held to bracket 43 by tie wire 22 such that tie wire tube 20 is perpendicular to arch wire 48 and generally parallel to the axis of tooth 31. Tie wire 22 passes through tie wire tube 20, is wrapped around orthodontic bracket 43, and is tied off at 50 outside of arch wire 48.

Curved surface 14 abuts arch wire 48, such that arch wire 48 is seated in notch 26. Curved surface 16 abuts tooth band 38. Spring end 24 is thus maintained in relatively close proximity to tooth 31 and away from the wearer's cheek or lip.

Installation of spring 10 is effected by positioning spring 10 in the space between arch wire 48 and tooth band 38 with arch wire 48 seated in groove 26. As tie wire 20 is tightened and tied off at 50, spring 10 is depressed within the space such that a force is exerted between arch 48 and tooth band 35. This force tends to cause rotation of tooth about its axis in the direction of arrow 35.

Removal of spring 10 is readily effected without having to disturb other appliances in the mouth by cutting tie wire 22 at any convenient place and removing spring 10 in a sequence that is the reverse of the installation sequence.

Tooth spring 10 may be made with any resilient material having the desired stiffness and elasticity. These particular properties of spring 10, as well as the physical dimensions, will depend on the particular application (e.g. size of tooth, necessary rotation of tooth, etc.).

It should be understood that the foregoing disclosure relates to a preferred embodiment of the invention, and admits of various modifications. For example, FIG. 4 shows an orthodontic rotation spring 10' which has curved surfaces 14' and 16' configured to present a generally U-shaped contour. The operation of the spring 10' is otherwise similar to that of spring 10 of FIGS. 1-3.

We claim:

1. An orthodontic spring for exerting a rotational torque on a patient's tooth, the tooth being fitted with a tooth band to which is fastened an orthodontic bracket adapted to receive an archwire, said spring comprising:
   a first generally planar spring segment having first and second ends;
   means for attaching said first end of said first spring segment to said bracket;
   a second generally planar spring segment extending at an angle from said second end of said first spring segment and toward said tooth, said second spring segment having a curved outer end portion;
   said first and second spring segments formed from a single length of spring material and having an outside surface generally facing said archwire and an inside surface opposite said outside surface;
   said outside surface at said second end of said first segment being biased against said archwire and said curved outer end portion of said second segment being biased against said tooth band, said outside surface having a recess to receive the archwire so that movement of said spring parallel to said outside surface is restricted, and said end portion being curved so that either said inside surface or said outside surface rests against said band, whereby said rotational torque is exerted on said tooth.

2. The orthodontic spring of claim 1 wherein said angle is an acute angle.

3. The orthodontic spring of claim 1 wherein said outer end portion is curved toward said bracket so that said outer surface is biased against the band.

4. The orthodontic spring of claim 1 wherein said outer end portion is curved away from said bracket so that said inner surface is biased against the band.

5. A orthodontic spring for exerting a rotational force on a patient's tooth, the tooth having an orthodontic bracket attached to a tooth band on the tooth, the bracket adapted to receive an orthodontic archwire, said spring comprising:
   an elongate, curved, relatively flat resilient body, said body having a bracket end and a tooth end;
   said bracket end having a tie wire tube formed thereto;
   said body having an inside surface generally facing said tooth and an outside surface opposite said inside surface;
   said resilient body having a central curved portion configured to bias the outside surface of said central portion against said archwire and the band end against the tooth whereby said rotational force is exerted on said tooth.
   said tooth end being curvedly formed so that either said inside or outside surface of said body is biased against said tooth; and
   said central portion having a cavity for receipt of said archwire therein so that movement of said body parallel to said outside surface is restricted.

6. The orthodontic spring of claim 5 wherein said body forms an acute angle at said central curved portion.

* * * * *